(12) United States Patent
Matthews

(10) Patent No.: US 6,494,919 B1
(45) Date of Patent: Dec. 17, 2002

(54) CRUTCH DEVICE

(75) Inventor: Lance Matthews, Mansfield (CA)

(73) Assignee: Canadaleg Inc. (CA)

( * ) Notice: Subject to any disclaimer, the term of this patent is extended or adjusted under 35 U.S.C. 154(b) by 0 days.

(21) Appl. No.: 09/647,623

(22) PCT Filed: Apr. 1, 1999

(86) PCT No.: PCT/CA99/00279
§ 371 (c)(1),
(2), (4) Date: Nov. 20, 2000

(87) PCT Pub. No.: WO99/51180
PCT Pub. Date: Oct. 14, 1999

Related U.S. Application Data

(60) Provisional application No. PCT/CA99/00279, filed on Apr. 1, 1999.

(51) Int. Cl.[7] .................................................. A61H 3/02
(52) U.S. Cl. .............................. 623/32; 623/27; 135/67; 135/77; 482/75
(58) Field of Search .............................. 623/27, 28, 32; 135/65, 68, 77; 482/75

(56) References Cited

U.S. PATENT DOCUMENTS

| | | | | |
|---|---|---|---|---|
| 2,678,054 A | * | 5/1954 | Bostelman | |
| 2,778,370 A | * | 1/1957 | Chamblee | 135/68 |
| 3,016,060 A | * | 1/1962 | Beattie | |
| 4,058,119 A | | 11/1977 | Rosequist | 128/80 R |
| 4,141,375 A | | 2/1979 | Tykwinski | 135/66 |
| 4,291,715 A | * | 9/1981 | Monte | 135/68 |
| 5,178,595 A | * | 1/1993 | MacGregor | 482/75 |
| 5,300,016 A | | 4/1994 | Marlatt | 602/16 |
| 5,514,054 A | * | 5/1996 | Rowan | 482/75 |
| 5,575,299 A | | 11/1996 | Bieri | 135/66 |
| 5,645,515 A | * | 7/1997 | Armstrong et al. | 482/75 |
| 5,941,263 A | * | 8/1999 | Bierman | 135/68 |
| D419,288 S | * | 1/2000 | Hartfield | D3/7 |

FOREIGN PATENT DOCUMENTS

| | | | |
|---|---|---|---|
| FR | 2643813 | | 9/1990 |
| WO | WO 8900039 | | 1/1989 |
| WO | WO 99/08645 | * | 2/1999 |

* cited by examiner

Primary Examiner—Robert Canfield
(74) Attorney, Agent, or Firm—Young & Basile, P.C.

(57) ABSTRACT

A prosthetic device for use with lower limb injuries, the device having a lower limb supporting platform and stabilizing brackets adjustably mounted on an upright leg member that is designed for efficient transfer of a user's weight through the hip, the upper leg and the knee to a foot disposed at the end of the leg member. The device allows the user to mimic a natural walking alignment preferably while maintaining the use of the arms and hands.

11 Claims, 10 Drawing Sheets

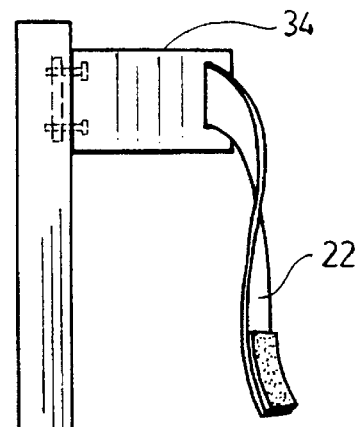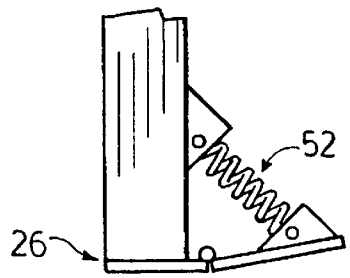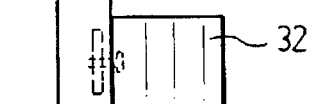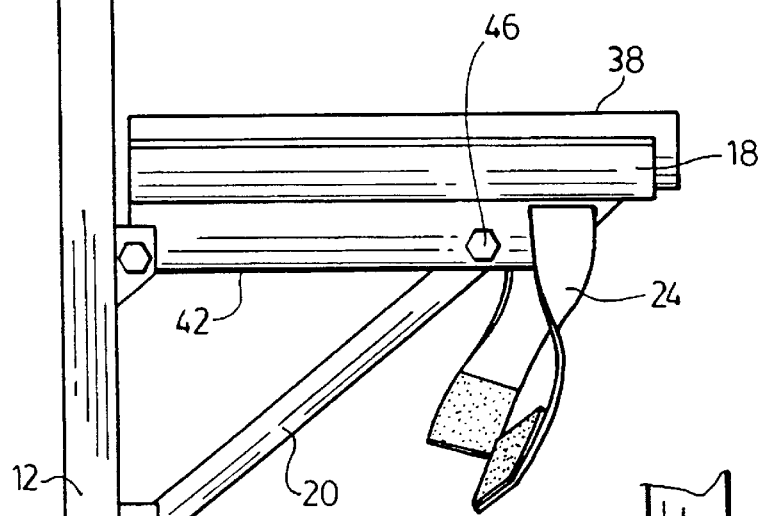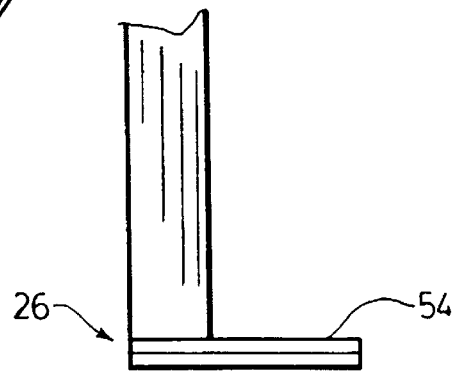
FIG. 4
FIG. 5
FIG. 6

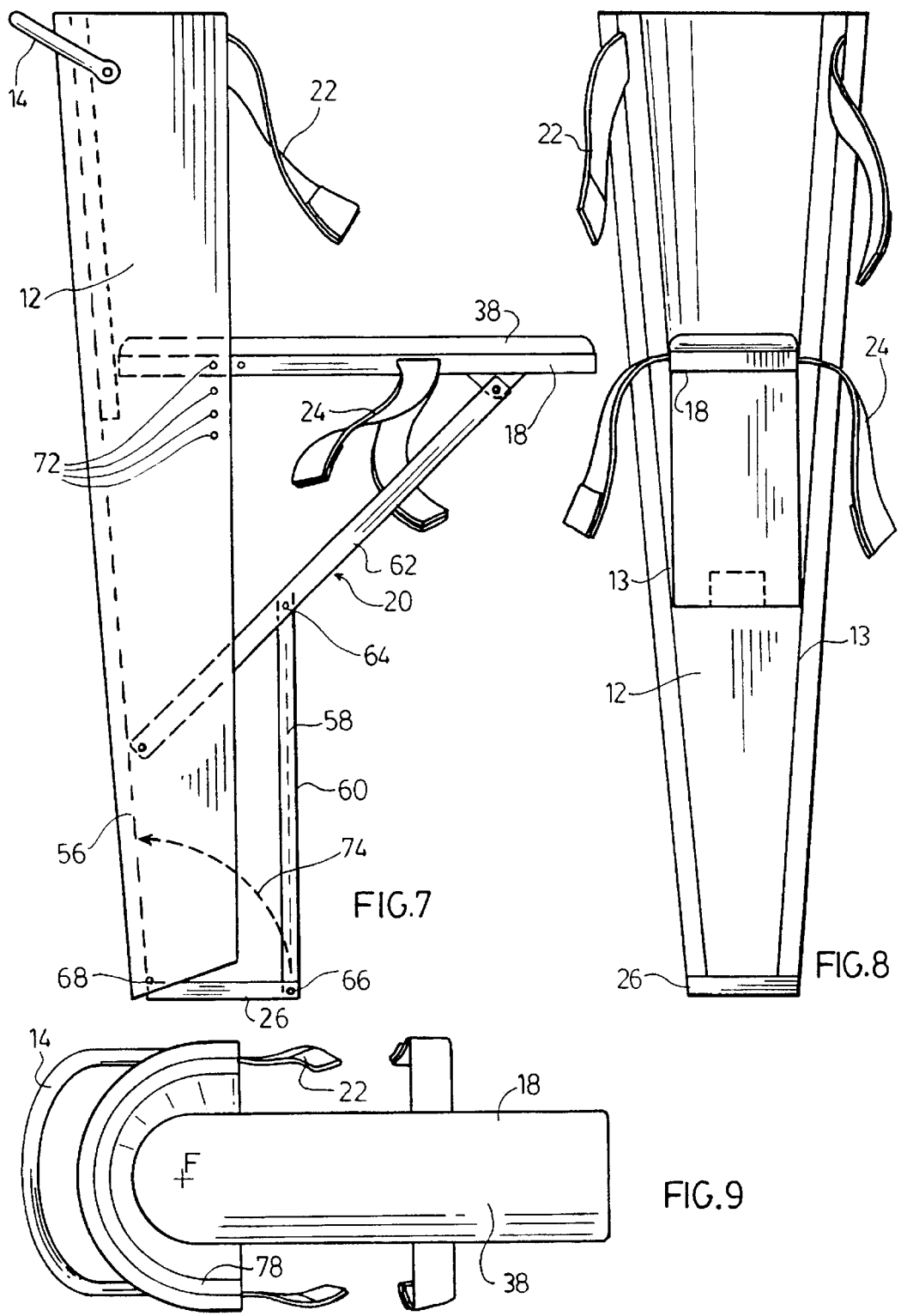

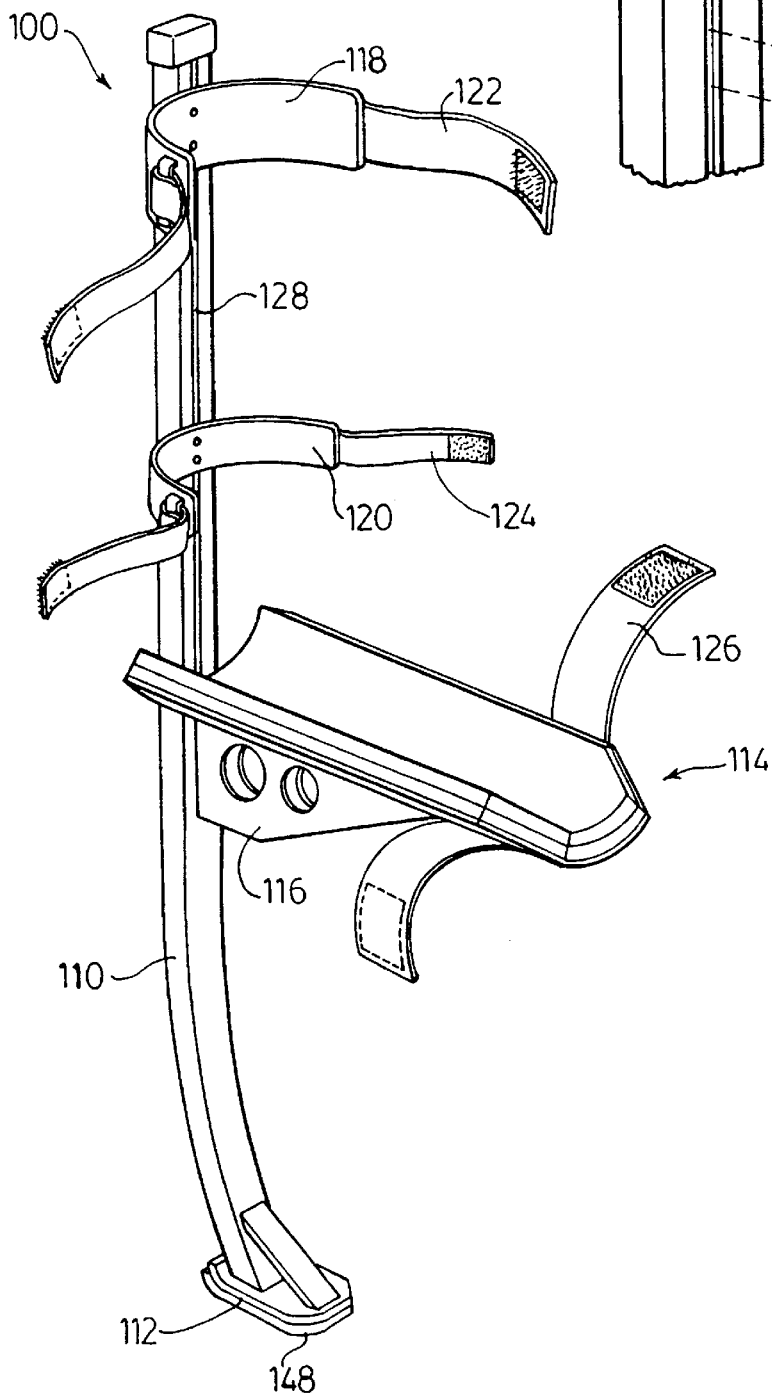

CRUTCH DEVICE

This application is a 371 of PCT/CA99/00279 filed Apr. 1, 1999.

FIELD OF THE INVENTION

The present invention is concerned with a crutch-like device designed to facilitate the ambulation of persons having non-weight-bearing lower leg injuries.

BACKGROUND OF THE INVENTION

Crutches have long been used as devices to assist those suffering from an injury to the lower extremities to walk. Traditional crutches extend from the shoulder/underarm to the ground to bear the weight of the injured person. Such crutches are usually fabricated from wood or light weight metal and comprise two upright shafts culminating at one end in a foot and being attached at the other end to a crossbar which is accommodated under the arm. A second crossbar at approximately the mid-point acts as a handle. There are several problems associated with these types of crutches including shoulder fatigue and the fact that it is necessary to use the muscles of the upper leg and lower back to support the lower leg in a slightly rearwardly upward manner to maintain sufficient clearance from the walking surface. This physical stature can result in painful muscle induced scoliosis. In addition, the hand or hands supporting the crutch(es) are not available for other activities. The center of gravity is also raised, thereby affecting balance.

The prior art has attempted to address the problems associated with crutches. U.S. Pat. No. 5,575,299, for example, discloses a walking device having a body member which can be attached to the lower leg. However, this device does not provide means for secure attachment to the upper limb and there may therefore be some rotation about the knee which gives a user a feeling of instability. U.S. Pat. No. 5,300,016 discloses a foldable prosthetic device which includes a shelf for supporting the lower leg. This device is complex to manufacture and has a plurality of components transferring weight along parallel axes. Both U.S. Pat. Nos. 5,575,299 and 5,300,016 result in strain being applied to an already injured limb and neither provide the degree of stability required for a user to comfortably maintain their balance.

The present invention overcome the problems of the prior art, including traditional crutches, by providing a support platform for the injured lower extremity affixed to an upright support leg such that the weight of the person is transferred through the hip, upper leg and knee rather than the shoulder and this therefore affords a more natural distribution as the center of gravity is lowered. This device can be attached to the upper leg and thigh to allow for single hand or hands free operation. The design of the present invention results in unexpected maneuverability and stability.

SUMMARY OF THE INVENTION

A crutch, particularly for non-weight-bearing lower leg and foot injuries, and adapted for optional single hand or hands-free operation is provided. The device provides for single hand or hands free operation by supporting the lower leg on a platform connected to an upright support and having means for attachment to the thigh and upper leg and locates the lower leg. The crutch has a platform on which the knee and lower leg, in a bent position, is supported. The forces applied to the platform are transmitted downwardly along a ground engaging upright leg support.

According to one aspect of the invention there is provided a walking device comprising an elongate, essentially vertical unitary leg member having an upper portion and a lower portion, an essentially horizontal support platform mounted on the leg member for supporting a user's knee and corresponding lower leg portion in a bent position; a stabilizing bracket mounted on the upper portion of said leg member to hold a user's upper leg in position, and a foot member at the end of the leg member, whereby the lower portion of the leg member is offset such that the extent of offset provides for a continuous longitudinal axis from the hip, through the upper leg and intersecting the foot member. This provides enhanced stability through alignment with the user's center of gravity. The unitary nature of the vertical leg ensures that a user's leg and the device move in unison.

In another aspect, the upright vertical leg member has at least one stabilizing bracket mounted thereon to align positioning of the upper leg and knee parallel to the upright leg member and to provide lateral sideways support. An attachment system is associated with the stabilizing bracket to secure the device to the user's leg. The lower leg is supported in a horizontal platform which also comprises an attachment system for securing the lower leg in position. The attachment system can take the form of velcro straps, leather belts, laces, or any other means of attachment.

In an aspect of the invention the support platform is mounted via a hinge to allow for collapse of the device along a single plane when not in use. The foot member of the device may include means for absorbing shock such as a rubber foot or a spring shock absorber. In another aspect of the invention, the foot is elongated to provide additional support.

The device may be fabricated from a metal such as aluminum or from wood, plastic, fiberglass or other light weight natural or synthetic materials. A handle may be provided on the front of the device to aid in pivoting the device when in use.

BRIEF DESCRIPTION OF THE DRAWINGS

Several aspects of the invention are illustrated in the accompanying drawings, in which like numerals denote like parts throughout the several views, and in which:

FIG. 4 is a side elevational view of the embodiment of FIG. 3;

FIG. 5 is a side view of one embodiment of the foot portion;

FIG. 6 is a side view of another embodiment of the foot portion;

FIG. 7 is a side view of a third embodiment;

FIG. 8 is a rear view of the embodiment of FIG. 7;

FIG. 9 is a top view of the embodiment of FIG. 7;

FIG. 10 is a perspective view of a preferred fourth embodiment;

FIG. 11 is an exploded partial view of the embodiment of FIG. 10;

DETAILED DESCRIPTION OF PREFERRED EMBODIMENTS

Crutches have traditionally been used to help those suffering from lower leg injuries to get around. However, crutches limit the use of the hands for other activities and are generally described as clumsy, tiring and uncomfortable.

Twelve weeks or more may pass between the time a person receives treatment and their recovery under the supervision of a therapist. During this time a healthy person with an injured limb loses a degree of fitness due to inactivity. The present invention allows the user to maintain a healthy level of physical activity and there may also be psychological benefits when the user is capable of independent movement.

The present invention is particularly applicable to otherwise healthy individuals who suffer a lower limb injury. The device is ideally suited to the recovery of injured workers, outdoor enthusiasts and athletes but is also applicable to patients with diabetes and other afflictions which affect circulation in the leg as well as for post-operative patients. The device also has special application for war victims such as land-mine survivors.

Thus, the present invention provides a prosthetic device for those suffering from lower leg, ankle and foot injuries of all types. The device affords a platform on which, preferably, the lower part of the leg below the knee is supported and an upright vertical support. The device takes advantage of the natural pivoting action provided in the hip and provides walking assistance by essentially rigidly extending the upper leg to a walking surface. The individual's weight is transmitted downwardly through the upper leg to the knee and along the device to the ground. The device can be easily adjusted to accommodate differences in height and weight and is attached to the leg to provide for hands-free operation. This device provides an attractive, more versatile alternative to traditional crutches.

Figure 1:
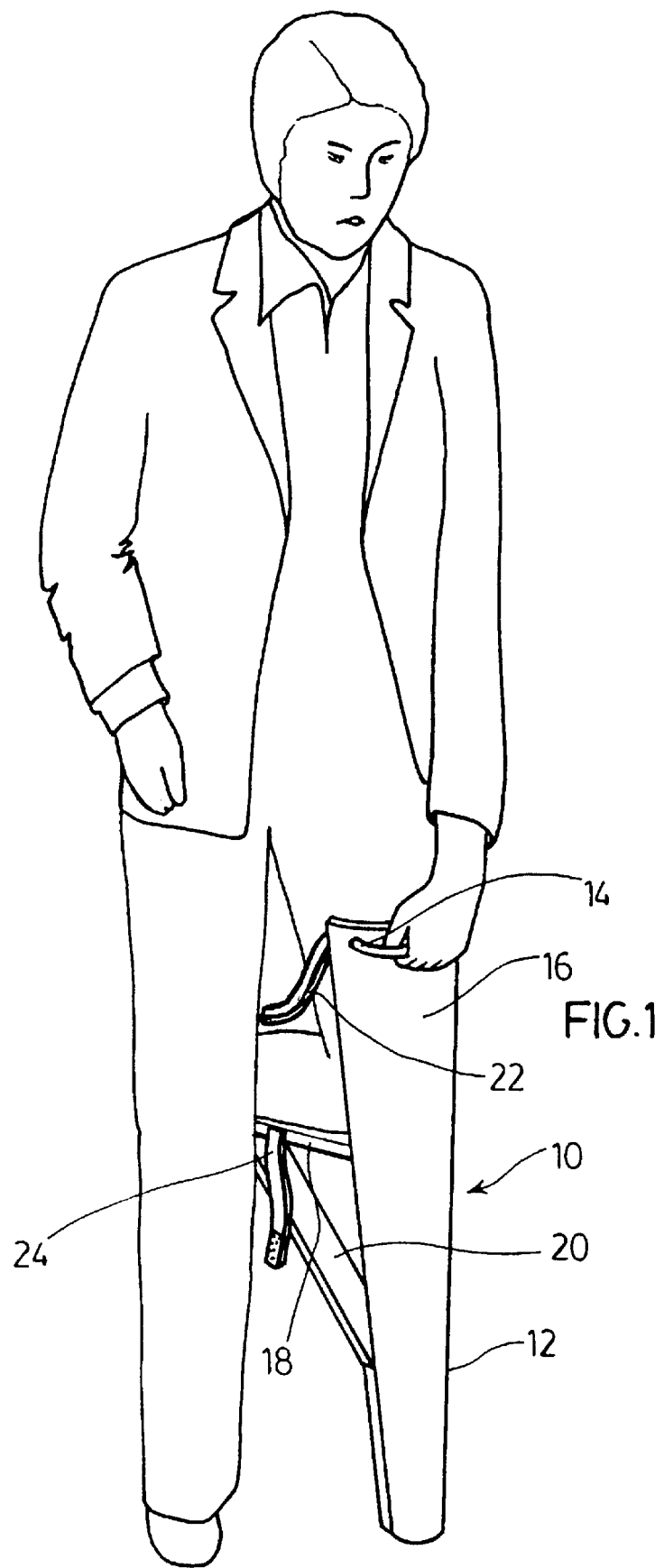
FIG. 1 is a schematic illustration demonstrating the use of one embodiment of the device.
Figure 2:
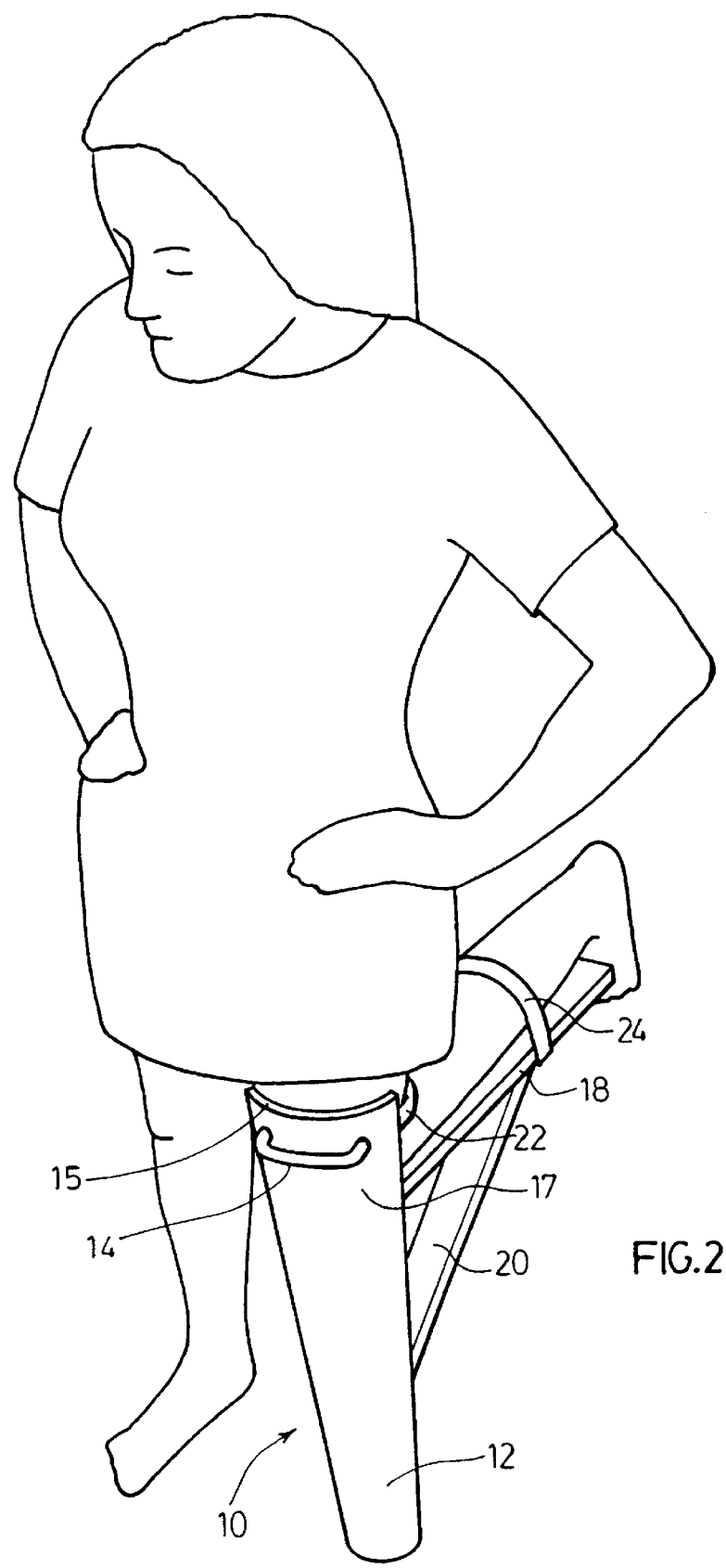
FIG. 2 is a schematic illustration demonstrating a hands-free mode of operation of the same embodiment.

Referring to FIG. 1, the use of one embodiment of the device 10 is shown. In this configuration an upright leg member 12 has a handle/pommel 14 on the outer conical surface 12. The horizontal platform member 18 is supported by a brace 20. FIG. 2 illustrates the device 10 secured to the leg by upper leg attachment means 22 and lower leg attachment means 24. The conical shape of the support at the regions 15 and 17 stabilize the upper leg and knee, respectively.

Figure 3:
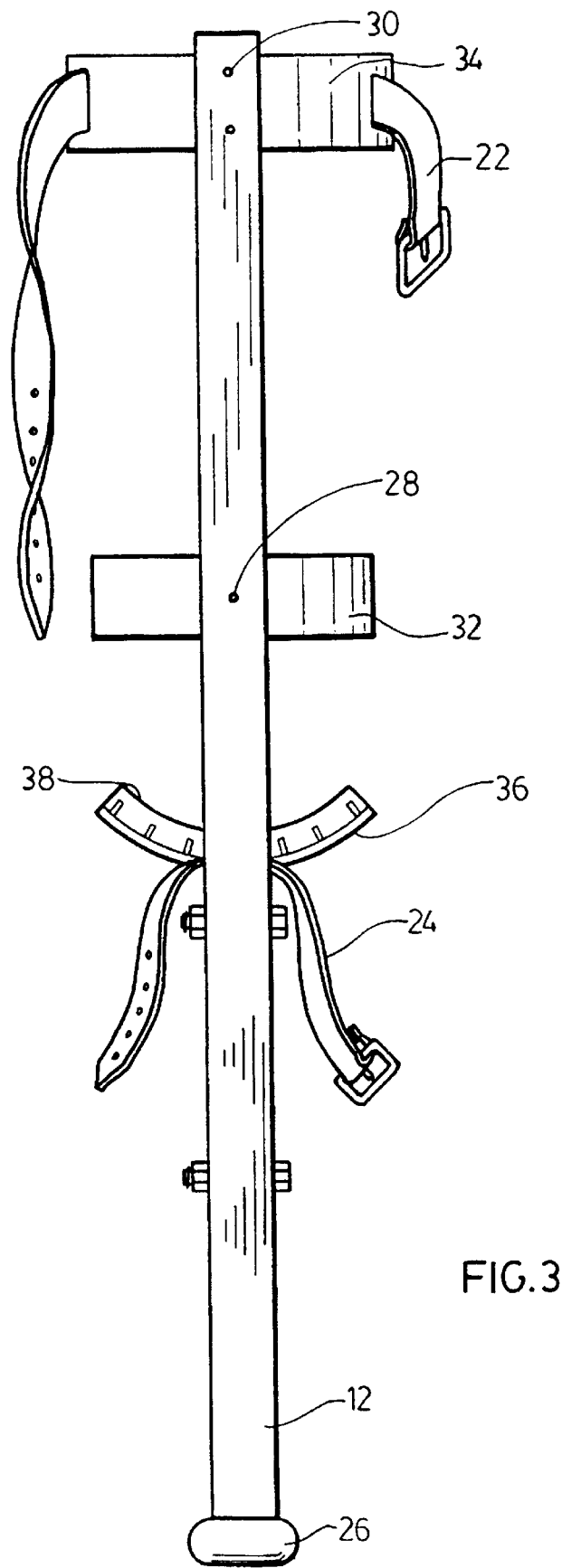
FIG. 3 front elevational view of a second embodiment.

In a preferred embodiment shown in FIG. 3, the device comprises a single upright leg member 12 which is essentially vertical when in use and which has a ground engaging foot 26. It is clearly apparent that the ground engaging foot can take various forms and is not limited to a "foot" per se. Preferably the foot will be shock-absorbing, slip resistant, friction enhancing, long lasting and replaceable. Attached perpendicularly by screws 28 and 30 are upper and lower brackets 32 and 34, respectively which function as and are part of a leg stabilizing system. It is clearly apparent that other stabilizing systems could perform the same function. The purpose of upper bracket 34 is to support and align the upper leg within the device while lower bracket 32 holds the knee in position.

The present invention has the advantage over standard prosthetic devices in that it is easily and rapidly adjusted for height. The positions of brackets 32 and 34 are adjustable vertically along the axis of the upright support member 12 to accommodate individuals of different heights. An upwardly opening cradle-like horizontal support platform 18 is also vertically adjustably affixed to the upright support member 12. The height of the components may be infinitely adjustable along the length of the upright leg member. Various means may be utilized for the adjustment. For example the brackets may be slidably mounted in a groove on the upright leg and the mounting may be adjusted through the use of a simple Allen key.

In one aspect of the invention, best seen in FIG. 4, the support platform 18 is provided with a cushioned surface 38 for added comfort. Upper leg attachment straps 22 are provided to secure the upper leg within bracket 32 in alignment with the axis of the upright support member 12. Knee attachment straps are provided on bracket 32. Lower leg attachment straps 24 secure the lower leg in a bent position to the support platform 18.

As seen more clearly with respect to FIG. 4, the horizontal platform 18 is mounted on an arm 42 which, when in use, is held in a position horizontal to the vertically upright support member 12 by means of a brace 20. The brace 20 is secured at one end to a vertically adjustable brace locator 43 via bolts 44. The other end of the brace is secured to the arm 42 by bolts 46. The arm 42 is secured to a vertically adjustable support locator by bolts. The brace locator 43 and the support locator can be adjusted vertically within a groove (not shown) on the inner surface of the leg member 12 to make corrections for individual differences in height. The brace 20 may be a foldable strut or other type of hinged brace to allow the arm 42 to pivot to a position parallel to the upright support member for storage. In one aspect of the invention the lower end of the upright support 12 is offset rearwardly to promote better balance. The foot member 26 is preferably shock absorbing with a no-slip, long lasting replaceable, grease and oil resistant surface. In one embodiment, the foot member 26 may include a foot 50 fabricated from a compressible material such as rubber to absorb shock and resist slipping. In another embodiment shown in FIG. 5, the foot member 26 is provided with a spring shock absorber 52. In yet another embodiment shown in FIG. 6, the foot member 26 includes an elongated horizontal surface 54 for additional stability.

In another aspect of the invention as illustrated with respect to FIGS. 7, 8, and 9, the upright support member 12 is rearwardly openly, essentially conical in cross-sectional shape. However, it is clearly apparent that the upright support function can be provided by many different configurations. Referring to FIG. 7 which shows a side view of a preferred embodiment, the upright leg member 12 has a handle 14 affixed to the front surface. The handle is used to aid in the pivotal movement of the device. The force of the weight applied to the support platform 18 is transmitted downwardly from the knee to the foot member 26 along two essentially vertical axes. Partial weight may be borne by a hand on a handle 14. One axis, indicated by the dashed line 56 is coaxial with the upright support member 12 while the other axis, indicated by the dashed line 58 is coaxial with an auxiliary upright member 60. The auxiliary upright member 60 is connected to an intermediate segment 62 of the leaf spring brace 20 by bolts 64 and to the foot member 26 by bolts 66. As described previously with respect to FIG. 4, one end of the brace is attached to the upright leg member 12 and the other end is attached to the arm 42. The other end of the foot member 26 is attached to the upright leg member 12 and made to fit inside an opening in the end of member 12. Rods associated with bolts 44, 64, hinge 66 and hinge 68 allow for pivotal motion around the bolts and, in combination with a leaf spring brace 20, accommodate folding of the unit when not in use. The position of the support platform 18 is adjustable vertically through a series of bolts 72. When in use, the upright support member 12 is held at a slight forward lean angle, as indicated by the arrows 74. This forward angling induces a more natural step motion and therefore provides for better balance. Forward angle on foot 26 also helps add rocking motion for improved step completion.

Referring now to FIG. 8, which is a rear view of the device, it is clearly apparent that the device could also be provided with two parallel upright supports 13 with the support platform 18 disposed in between. FIG. 9 illustrates a top view showing the handle 14 on the outer surface of the upright support 12. Padding 78 is fitted to the inside surface for added comfort. The base of the horizontal support platform 18 is also provided with a cushioned surface 38.

Figure 12:
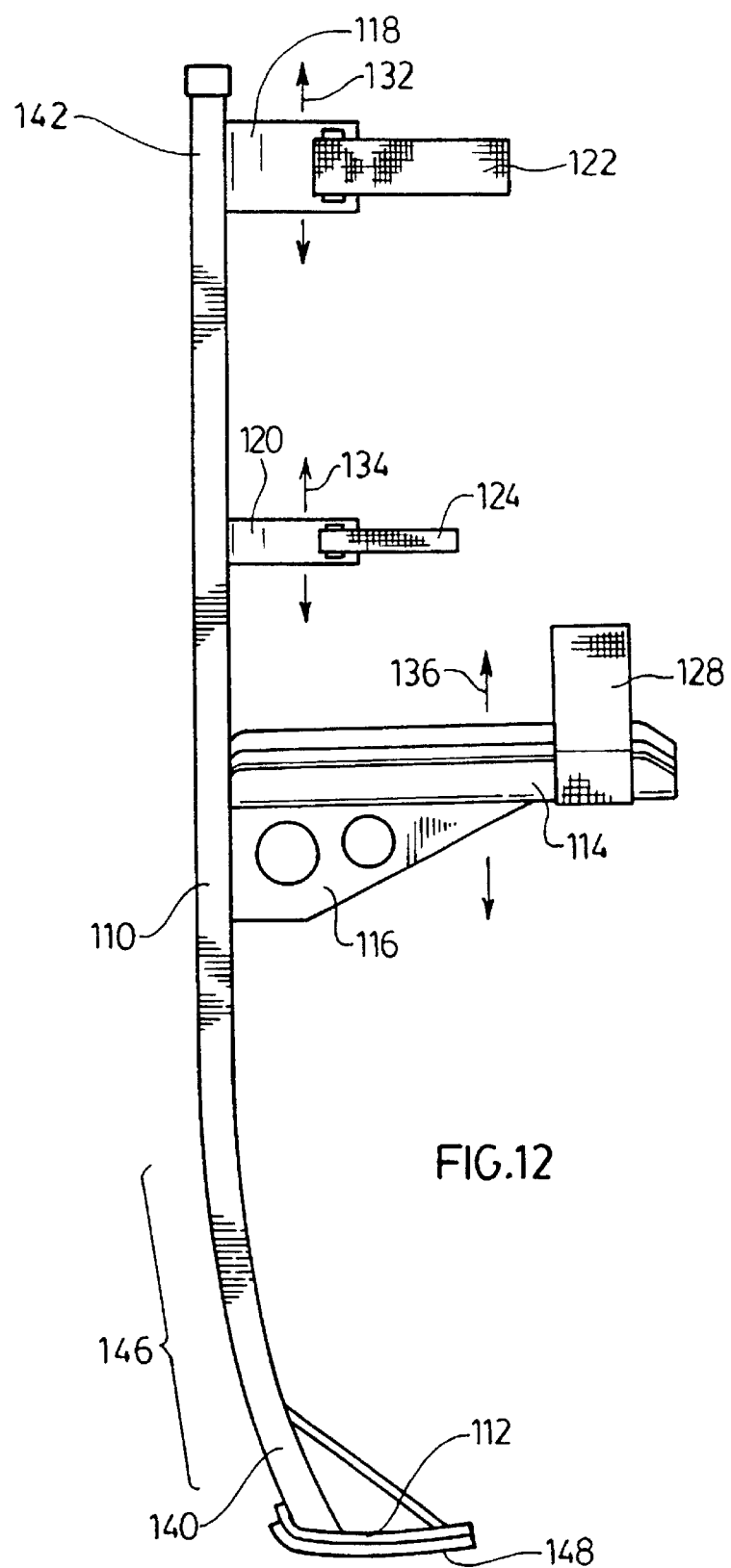
FIG. 12 is a side view of the embodiment shown in FIG. 10.
Figure 13:
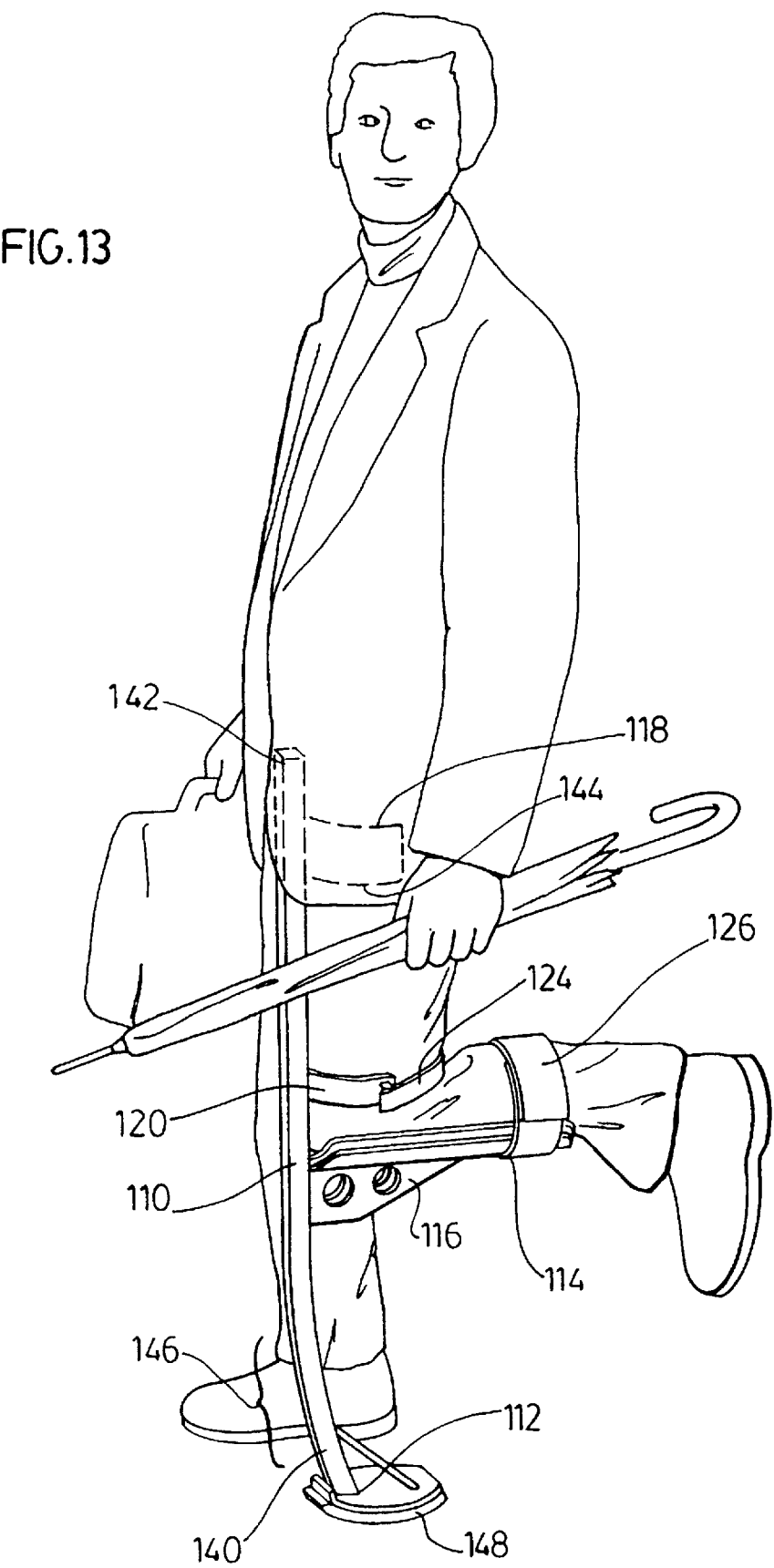
FIG. 13 is a perspective view of the device of FIG. 10 in use.

FIGS. 10 through 13 illustrate another preferred embodiment of the invention. The device 100 comprises an upright leg member 110 terminating in a foot member 112, a horizontal platform 114 supported by a brace 116, and upper 118 and lower 120 stabilizing brackets. Upper leg attachment straps 122, knee attachment straps 124 and lower leg attachment straps 126 are also provided. The stabilizing brackets 118, 120 are mounted in a longitudinal groove 128 in the upright leg member 110 by screws as illustrated in FIG. 11. FIG. 12 illustrates a side view of this embodiment of the device 100 in which arrows 132, 134, 136 indicate that the upper stabilizing bracket 118, the lower stabilizing bracket 120 and the horizontal platform brace 116 respectively are slidably, vertically adjustable along the longitudinal groove thus allowing the device to be easily and quickly adjusted to fit people of different heights.

The upright leg member is designed to be integral with the user's leg. By positioning the leg member along the front of the user's leg, the natural axis of the leg is maintained. The positioning of the leg member along the front portion of a user's leg has the advantage of mimicing a natural walking alignment as compared to devices where the leg member is mounted along and to the side of the user's leg. The use of a single continuous leg member also provides for surprising stability as compared with prior art devices where the lower part of the leg member is either releasably connected to or hingedly connected to the upper part of the leg member. Because the leg member is securely held in place by the attachment straps such that the knee cannot be lifted from the platform plus the fact that the stabilizing brackets prevent sideways movement, the leg member moves in unison with the user's upper leg and a natural pivot and roll through gait can be accomplished. A surprisingly smooth gait can be achieved when the foot member is offset rearwardly of the upper front portion of the leg member. Preferably the extent of offset is sufficient so that the foot member hits the ground approximately where the heel would normally contact the ground. The device has the further advantage of allowing the user to ambulate without requiring use of the arms. This advantage permits the user to carry on with normal duties.

In a preferred embodiment, the upright leg member 110 is fabricated as a single light weight continuous strut wherein the lower end 140 of the strut is offset rearwardly relative to the upper end 142 of the strut. The extent of the offset is sufficient to bring the foot member 112 into vertical alignment with the hip, the upper leg and the knee. The longitudinal axis so defined is designated as 144 on FIG. 13. This alignment causes the upper leg and the leg member to pivot in unison. In addition, this alignment causes the user's body weight to be transferred through the hip and knee which are natural weight bearing joints as opposed to the shoulder and underarm which bear the weight when traditional crutches are used. The alignment prevents muscle fatigue by ensuring that the joints and limbs function as naturally as possible. The extent of offset provides for a natural rolling gait since the foot member contacts the ground in such a manner that the weight is naturally transferred.

In a preferred embodiment, the natural gait, which is facilitated by the offset of the foot member is further enhanced when the leg member 110 is designed to have an integral controlled degree of flexure. The leg member 110 is designed to provide torsional rigidity so that it does not twist about the longitudinal axis when the device is being used. The construction material should, however, be selected to allow for controlled resilient flex along the lower part of the leg member to provide thereby an inherent flex region which absorbs energy as the foot member contacts the ground. With respect to the drawings, when weight is transferred along the length of the leg member, the leg member resiliently flexes slightly in region 146 to act as a shock absorber during walking to prevent a jarring motion every time the foot member 112 hits the ground. This controlled flexing is achieved by the offset feature of the leg member design which provides a transition region 146 for transmitting forces to the foot member 112.

The foot member 112 may be slightly upturned at the front and rear to facilitate a more normal rolling type of gait when the device is used. The lower surface 148 preferably comprises a non-slip material.

Figure 14:
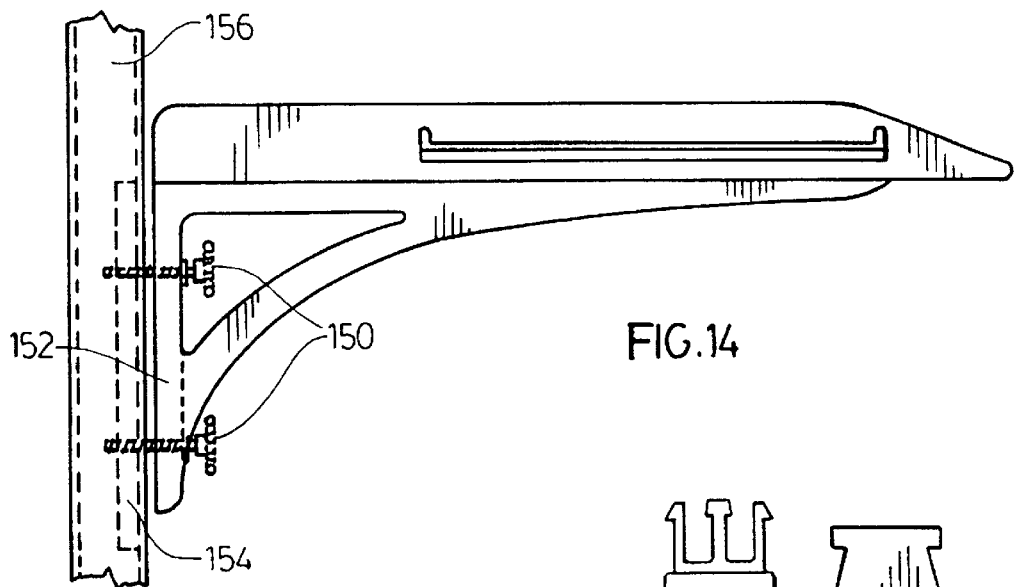
FIG. 14 is a partially cut away side elevational view of a preferred fifth embodiment.

Part, or all, of the device may also be constructed from a synthetic material such as reinforced plastic. FIG. 14 illustrates an embodiment in which plastic hand screw adjustors 150 can be utilized to anchor the horizontal platform brace 152 to an anchor block 154 on the upright leg member 156.

Figure 15:
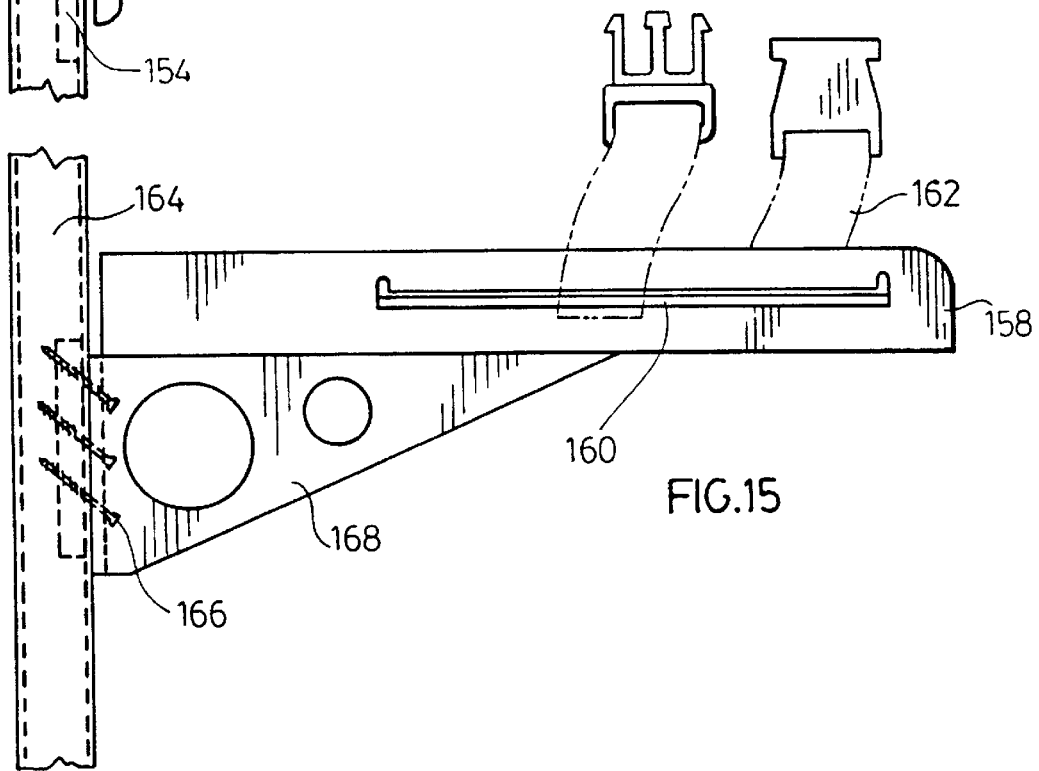
FIG. 15 is a partially cut away side elevational view of an alternative embodiment.

As shown in FIG. 15, the horizontal support platform 158 may be adapted to provide a horizontal groove 160 along which the lower leg attachment straps 162 can slide and thus secure the lower leg at a preferred location. It is clearly apparent that more than one set of attachment straps may be provided. In this embodiment, the horizontal platform 158 is mounted to a vertical leg member 164 by means of screws 166 on a brace 168. This embodiment is particularly useful in situations where a user may have lost part of the lower limb.

Figure 16:
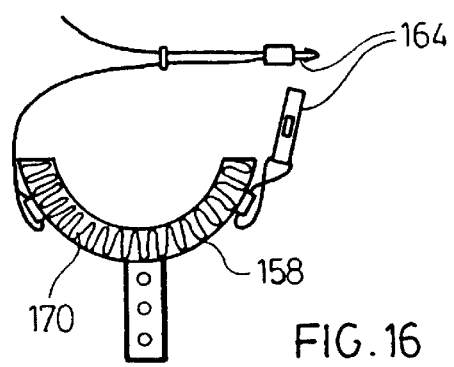
FIG. 16 is an end view of the horizontal platform.

FIG. 16 shows an end view of the horizontal support platform 158. The platform 158 is lined with a compressible material 170 for added comfort. The ends of the securing means 162 may be attached together by an adjustable slide release buckle 164, as illustrated, or by various other means such as velcro or various types of belt buckles.

Figure 17:
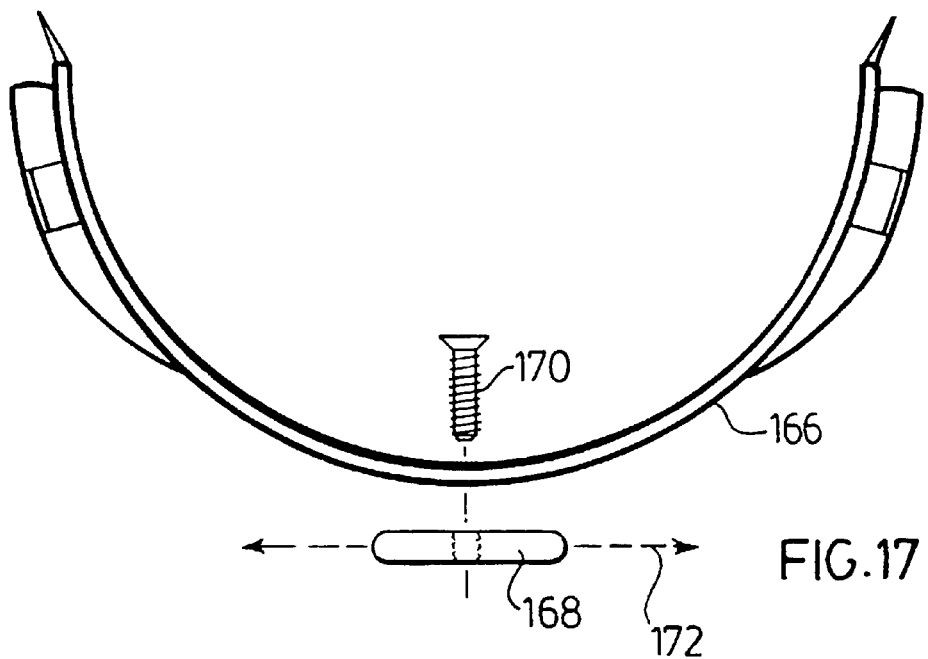
FIG. 17 is a top view of a stabilizing system.
Figure 18:
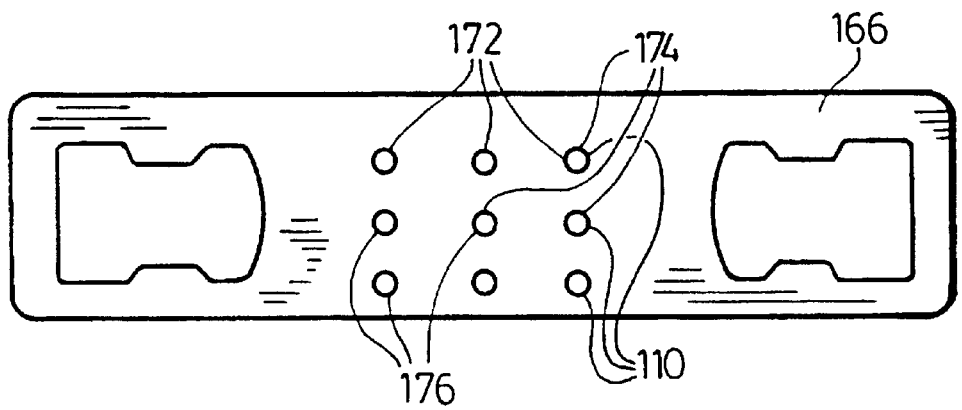
FIG. 18 is a front view of a stabilizing system.

An alternative arrangement for the attachment of the upper and/or lower stabilizing bracket 166 to the upright leg member is shown in FIG. 17. A floating anchor block 168 is provided in the leg member so that the screw adjustors 170 which anchor the bracket 166 can be shifted along a traverse axis 172. This arrangement is particularly useful in cases where the upper limb may be deformed in some manner due to reconstruction or various other reasons. For example, the upper leg may naturally tilt either outwardly or inwardly. A front view illustrating how the stabilizing means may be adjustably positioned along two planes is shown in FIG. 18. The vertical adjustment may be altered by selecting a series of vertical adjustment bores 170 for attachment of the bracket. The horizontal adjustment may be altered by selecting a series of horizontal adjustment bores 172. For example, referring to FIG. 18 the bracket could be mounted via the upper right hand bores 174 or via the lower left hand bores 176 or anywhere in between such that the bracket may or may not be mounted such that its cross-sectional axis is perpendicular to the axis of the leg member.

Although preferred embodiments of the invention have been described herein in detail, it will be understood by those skilled in the art that variations may be made thereto without departing from the spirit of the invention.

I claim:

1. A prosthetic device comprising:
   i) an elongate, essentially vertical unitary leg member having an upper portion and a lower portion, wherein said leg member is a single continuous strut;
   ii) an essentially horizontal support platform mounted on said leg member for supporting a user's knee and corresponding lower leg portion in a bent position;
   iii) stabilizing means mounted on said upper portion of said leg member to hold a user's upper leg in position;
   iv) attachment t means associated with said stabilizing means and said support platform to secure said device to a user's leg, and
   v) a foot member at an end of said lower portion of said leg member wherein said lower portion of the leg member is offset such that the extent of offset provides for a continuous longitudinal axis from a user's hip, through the upper leg and intersecting the foot member and whereby the unitary nature of the vertical leg member ensures that a user's leg and said device move in unison.

2. The device of claim 1 wherein said strut has inherent resiliency for flexibility along its lower portion and torsional rigidity to prevent rotation along its length.

3. The device of claim 2 wherein said leg member is fabricated from light weight metal.

4. The device of claim 2 wherein said leg member is fabricated from a synthetic material.

5. The device of claim 1 wherein the support platform has lower leg securing means attached thereto.

6. The device of claim 1 wherein said foot member includes a non-slip lower surface.

7. A prosthetic device comprising:
   i) an elongate, essentially vertical unitary leg member having an upper portion and a lower portion,
   ii) an essentially horizontal support platform mounted on said leg member for supporting a user's knee and corresponding lower leg portion in a bent position;
   iii) stabilizing means mounted on said upper portion of said leg member to hold a user's upper leg in position, wherein the support platform and the stabilizing means are slidably, vertically adjustable along said leg member;
   iv) attachment means associated with said stabilizing means and said support platform to secure said device to a user's leg, and
   v) a foot member at an end of said lower portion of said leg member wherein said lower portion of the leg member is offset such that the extent of offset provides for a continuous longitudinal axis from a user's hip, through the upper leg and intersecting the foot member and whereby the unitary nature of the vertical leg member ensures that a user's leg and said device move in unison.

8. The device of claim 7 wherein the stabilizing means comprises at least one circular bracket.

9. The device of claim 8 wherein the stabilizing means comprises an upper bracket to hold the upper leg in position and a lower bracket to hold the knee in position.

10. The device of claim 9 wherein the foot member is upwardly curved at least one end.

11. The device of claim 7 wherein said support platform is adjustably horizontally positionable.

* * * * *